US009675673B2

(12) United States Patent
Alt

(10) Patent No.: US 9,675,673 B2
(45) Date of Patent: Jun. 13, 2017

(54) TRANSLUMINAL DELIVERY OF ONCOLTYIC VIRUSES FOR CANCER THERAPY

(75) Inventor: Eckhard U. Alt, Houston, TX (US)

(73) Assignee: INGENERON INCORPORATED, Houston, TX (US)

( * ) Notice: Subject to any disclaimer, the term of this patent is extended or adjusted under 35 U.S.C. 154(b) by 873 days.

(21) Appl. No.: 12/766,776

(22) Filed: Apr. 23, 2010

(65) Prior Publication Data
US 2010/0331815 A1 Dec. 30, 2010

Related U.S. Application Data

(60) Provisional application No. 61/184,280, filed on Jun. 4, 2009, provisional application No. 61/172,263, filed on Apr. 24, 2009.

(51) Int. Cl.
A61K 48/00 (2006.01)
A61K 38/21 (2006.01)
A61K 35/768 (2015.01)

(52) U.S. Cl.
CPC ............ *A61K 38/21* (2013.01); *A61K 35/768* (2013.01); *A61K 48/0075* (2013.01); *A61M 2202/206* (2013.01); *C12N 2750/14332* (2013.01)

(58) Field of Classification Search
CPC .. A61K 38/21; A61K 35/768; A61K 48/0075; A61K 2300/00; C12N 2750/14332; A61M 2202/206
USPC .............................. 424/85.4, 93.6; 435/235.1
See application file for complete search history.

(56) References Cited

U.S. PATENT DOCUMENTS

| 4,689,041 | A | * | 8/1987 | Corday et al. ................ 604/509 |
| 5,328,470 | A | * | 7/1994 | Nabel .................... A61B 17/22 |
| | | | | 604/101.03 |
| 5,585,254 | A | * | 12/1996 | Maxwell .............. C07K 14/005 |
| | | | | 424/405 |
| 5,646,185 | A | * | 7/1997 | Giaccia .................. A61K 31/00 |
| | | | | 514/548 |
| 6,489,307 | B1 | * | 12/2002 | Phillips .............. C12N 15/1138 |
| | | | | 435/320.1 |
| 6,805,860 | B1 | | 10/2004 | Alt |
| 7,179,456 | B2 | | 2/2007 | Rommelaere et al. |
| 7,452,532 | B2 | | 11/2008 | Alt |
| 2002/0055721 | A1 | * | 5/2002 | Palasis ...................... A61L 2/18 |
| | | | | 604/265 |
| 2002/0095114 | A1 | * | 7/2002 | Palasis ....................... 604/96.01 |

(Continued)

OTHER PUBLICATIONS

Ponnazhagan, "Parvovirus Vectors for Cancer Gene Therapy", Expert Opin. Biol. Ther. (2004) 4(1):53-64.*

(Continued)

Primary Examiner — Nathan R Price
Assistant Examiner — Gerald Landy, II

(57) ABSTRACT

Methods, apparatus and compositions are provided for treatment of cancer of a selected organ by intraluminal delivery of oncolytic agents through a blood vessel or duct leading to the cancer tissue. During the time the oncolytic agents are being applied to the targeted tissue downstream, the designated vessel or duct can be selectively occluded to increase concentration and pressure of the applied agents at the target site. Oncolytic compositions including oncolytic viruses formulated with delivery visualization markers are provided.

13 Claims, 3 Drawing Sheets

(56) References Cited

U.S. PATENT DOCUMENTS

| | | | |
|---|---|---|---|
| 2002/0155432 A1* | 10/2002 | Schwartz | A61K 48/0058 435/5 |
| 2004/0076622 A1* | 4/2004 | Studeny | C12N 15/86 424/93.21 |
| 2007/0244367 A1 | 10/2007 | Caffey et al. | |
| 2008/0249400 A1 | 10/2008 | Golijanin et al. | |
| 2008/0306570 A1* | 12/2008 | Rezai | A61N 1/0553 607/42 |
| 2009/0060886 A1 | 3/2009 | Alt | |

OTHER PUBLICATIONS

Boekstagers et al; Myocardial gene transfer by selective pressure-regulated retroinfusion of coronary veins; Gene Therapy; 2000; pp. 7:232-7:240.

Cotmore et al; The autonomously replicating parvoviruses of vertebrates; Adv Virus Res ; 1987; pp. 33:91-33:174.

Di Piazza et al; Cytosolic activation of cathepsins mediates parvovirus H-1-induced killing of cisplatin and TRAIL-resistant glioma cells; J Virol ; 2007; pp. 81:4186-98.

Fong et al; A Herpes Oncolytic Virus Can Be Delivered Via the Vasculature to Produce Biologic Changes in Human Colorectal Cancer; Am. Soc. Gene Therapy; 2009; pp. 17(2):389-394.

Haag et al; Highly efficient transduction and expression of cytokine genes in human tumor cells by means of autonomous parvovirus vectors; generation of antitumor responses in recipient mice; Hum Gene Ther; 2000; pp. 11:597-11:609.

Hecht et al; A phase I/II trial of intratumoral endoscopic ultrasound injection of ONYX-015 with intravenous gemcitabine in unresectable pancreatic carcinoma; Clin Cancer Res ; 2003; pp. 9:555-61.

Liu et al; Systemic Efficacy with Oncolytic Virus Therapeutics: Clinical Proof-of-Concept and Future Directions; Cancer Res.; 2007; pp. 67(2):429-432.

Makower et al; Phase II Clinical Trial of Intralesional Administration of the Oncolytic Adenovirus ONYX-015 in Patients with Hepatobiliary Tumors with Correlative p53 Studies; Clinical Cancer Research ; 2003; pp. 9:693-702.

Rommelaere et al; Antineoplastic activity of parvoviruses; J Virol Methods ; 1991; pp. 33:233-51.

Sieben et al; Killing of p53-deficient hepatoma cells by parvovirus H-1 and chemotherapeutics requires promyelocytic leukemia protein; World J. Gastroenterology; 2008; pp. 14(24):3819-3828.

Takaoka et al; Integration of interferon-a/I1 signalling to p53 responses in tumour suppression and antiviral defence; Nature; 2003; pp. 424:516-523.

Wollmann et al; Targeting Human Glioblastoma Cells: Comparison of Nine Viruses with Oncolytic Potential; J. Virol.; 2005; pp. 79(10):6005-6022.

* cited by examiner

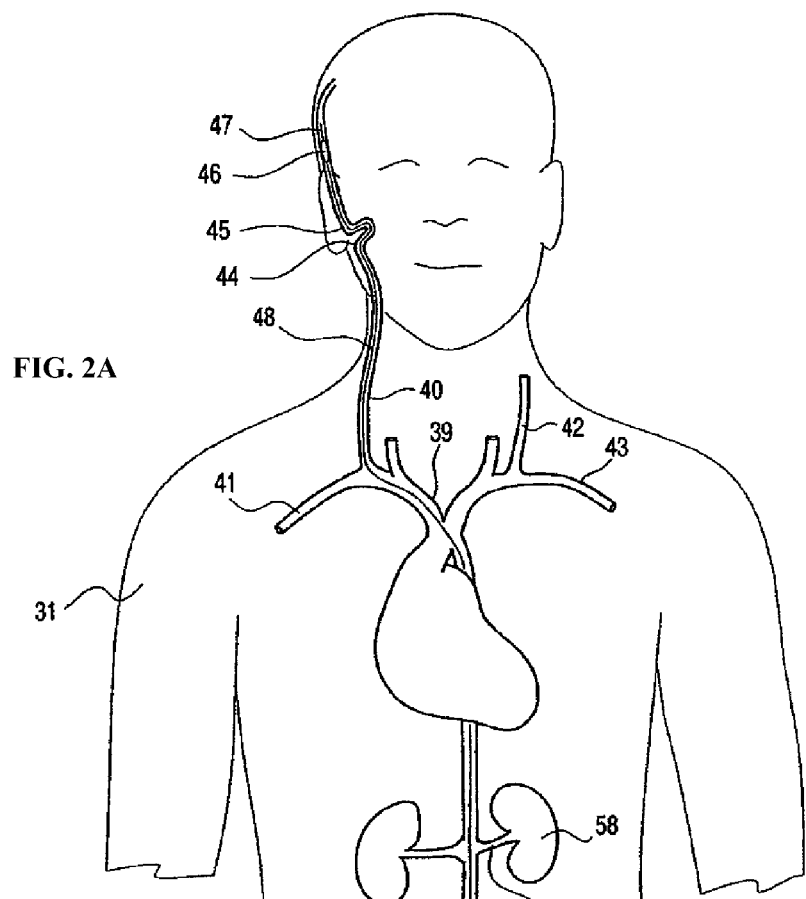
FIG. 2A
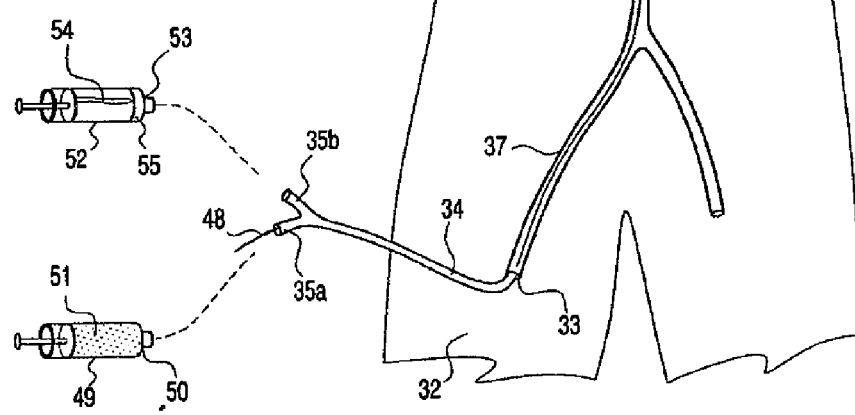
FIG. 2C
FIG. 2B

TRANSLUMINAL DELIVERY OF ONCOLTYIC VIRUSES FOR CANCER THERAPY

CROSS-REFERENCE TO RELATED APPLICATIONS

This application claims priority to U.S. Application Ser. No. 61/172,263, filed on Apr. 24, 2009, and U.S. Application Ser. No. 61/184,280, filed on Jun. 4, 2009. The disclosures of the prior applications are considered part of (and are incorporated by reference in) the disclosure of this application.

FIELD OF THE INVENTION

This invention relates to compositions and methods for treatment of tumors with oncolytic viruses in conjunction with supportive agents to enhance the function of the virus.

BACKGROUND OF THE INVENTION

Without limiting the scope of the invention, its background is described in connection with existing tumor treatments.

Given that tumor cells are derived from normal cells and share basic metabolic features with the normal cells from which they are derived, selective destruction of tumor cells is in most cases a balance between relative toxicity to tumor versus normal cells. While the successful treatment of certain cancers has come within reach, tumors such as for example glioblastoma and pancreatic cancer remain particularly difficult to treat and are typically associated with a dire prognosis.

Indeed, pancreatic cancer is one of the most lethal of gastrointestinal malignancies. Pancreatic cancer is the fourth most frequent cause of cancer-related deaths in North America, the sixth in Europe, and the fifth in the UK. The disease is highly resistant to currently available treatments. Surgical resection provides the best possibility for long-term survival, but is feasible in a minority of patients only and is not without risk. In advanced disease where surgery is not an option, chemotherapy comes into play, using in particular gemcitabine or 5-FU (5-fluorouracil), although the effects are still modest and always accompanied by high general toxicity. Malignant glioma is another one of the highly lethal human cancers. With conventional treatment of surgery, radiation and chemotherapy, the average life span after diagnosis is 12-16 months.

Cancer therapy using viruses or armed vector derivatives that specifically kill neoplastically transformed cells (oncolysis) is a novel approach to the treatment of certain cancers. Oncolytic viruses, which by definition preferentially infect and/or kill cancer cells, include certain members of a number of the virus families including herpesviridae (i.e. HSV, CMV and pseudorabies), poxviridae, adenoviridae, parvoviridae, rhabdoviridae (i.e. vesicular stomatitis virus), togaviridae (Sindbis) and picornaviridae (i.e. coxsackie virus and poliovirus).

A recent therapy for pancreatic cancer and other carcinomas has included delivery of an adenovirus that is selectively oncolytic for TP-53 deficient pancreatic tumor cells. See Hecht J R, et al. "A phase I/II trial of intratumoral endoscopic ultrasound injection of ONYX-015 with intravenous gemcitabine in unresectable pancreatic carcinoma." *Clin Cancer Res* 9 (2003) 555-61. A phase II trial of intralesional administration of ONYX-015 for treatment of hepatobiliary carcinoma has also been undertaken and showed the treatment to be safe and well tolerated with modest evidence of clinical benefit. See Malkower D. et al. "Phase II Clinical Trial of Intralesional Administration of the Oncolytic Adenovirus ONYX-015 in Patients with Hepatobiliary Tumors with Correlative p53 Studies" *Clinical Cancer Research* 9 (2003) 693. In 2005, Shanghai Sunway Biotech's genetically modified adenovirus H101, which is closely related to ONYX-015, became the first oncolytic virus to be approved by a regulatory agency for the treatment of head and neck cancer.

Human glioblastoma tumor cell lines have been found to be particularly susceptible to infection by oncolytic parvoviruses. Treatment of human gliomas with such parvoviruses by local intratumoral delivery via steriotactic surgical injection, neuronavigation targeting, and by placement of an implanted catheter connected to a low flow pump has been suggested. See Rommelaere et al U.S. Pat. No. 7,179,456. Other viruses shown to be particularly active against glioblastomas include Vesicular Stomatitis Virus (VSV) and Sindbis virus. See Wollman et al. Targeting Human Glioblastoma Cells: Comparison of Nine Viruses with Oncolytic Potential. *J. Virol.* 79 (10) (2005) 6005-6022.

Despite the impressive results achieved with oncolytic agents, the anticancer effects of such agents could be improved, particularly as to routes of administration.

BRIEF SUMMARY OF THE INVENTION

The present invention is directed to methods and apparatuses for delivery of oncolytic viruses or cytostatic/toxic agents directly to tumors via natural fluid conduits leading to or from the immediate vicinity of the tumor, and to methods of increasing the local concentration of the viral or cytostatic/toxic agents at the tumor site. In one aspect, one or more interferons are co-administered locally together with the oncolytic viruses. In other aspects, interferons are administered in conjunction with oncolytic viral therapy. For example, the interferon may be administered at several time points including one or more of before, during and after delivery of the virus. In one aspect, delivery of oncolytic viruses to the cancer area is through one or more of the vascular tree of arteries, arterioles, capillaries, post capillary venules and veins, and/or the respective ductal system of the organ that supplies fluids to or drains the cancer area.

In other aspects, loco-regional delivery of interferon is provided by catheter delivery to the liver for treatment of hepatitis. In one embodiment, the interferon is provided in a slow release form. In other embodiments, an arterial catheter is placed via the gastroduodenal artery in the hepatic artery for the periodic scheduled delivery of interferon loco-regionally over a prolonged period. Locally high interferon concentrations are in some instances augmented by delivery of antiviral medications orally or by intravenous delivery.

In one embodiment, a method for cancer therapy is provided including delivery of an oncolytic virus by an intraluminal application through a blood vessel or duct, and, preferably, by occluding a lumen of the blood vessel or duct proximal to the location of viral egress from a delivery catheter such that concentration of viruses to the desired site can maximized. The intraluminal application of viruses through a blood vessel may be performed through an arterial or venous vessel or a duct depending on the target organ. The intraluminal application may be performed in a retrograde manner through the blood vessel or duct. In one aspect a balloon catheter is employed for the intraluminal application, and the occlusion of the blood vessel or duct is performed by inflating the balloon of the catheter for a time interval prescribed to increase the concentration of virus particles delivered to the local site. In other embodiments, the viral agents are delivered with pressure sufficient to cause extravasation of agent from the delivery vessel or duct and into the tissue. In one embodiment, a guide wire is introduced through the blood vessel or duct to the site, and thereafter the catheter is advanced over the guide wire until the distal end of the catheter reaches a selected point in the vicinity of the site for delivering the viruses. In one particular embodiment the oncolytic virus is a parvovirus.

Any cancer can be treated by the method and apparatus of the present invention provided the cancer is susceptible to infection by the selected oncolytic virus and is accessible via a body vessel or duct. Examples of such cancers include tumors that are well supported by blood vessels, including pancreatic cancer, prostate carcinoma, lung cancer, renal cancer, liver cancer, lymphoma, breast cancer, and brain tumors such as glioma, medulloblastoma and meningioma.

In one embodiment an occlusion balloon of an over the wire type catheter is inflated at the site of the primary injection, after the vessel has been cannulated. While the lumen of the vessel or duct is blocked, the oncolytic viruses are supplied by application through the balloon catheter over a relatively short period of time, on the order of 10 seconds to 15 minutes, for example depending on one or more of the size of the organ, its vascularisation, the viscosity of the virus carrier, and the type of tumor. Increased pressure sufficient to overcome the integrity of the lumen walls may be achieved by either more rapid delivery or increased volume over time. The viruses are injected through the inner lumen of the catheter while the balloon is inflated and the local pressure in the respective compartment is selectively increased in order to decrease potential washout of the virus.

BRIEF DESCRIPTION THE DRAWINGS

For a more complete understanding of the present invention, including features and advantages, reference is now made to the detailed description of the invention along with the accompanying figures:

FIG. 2A is a transparent front view of a patient illustrating an exemplary procedure for injecting oncolytic biologic agents into the cerebral circulation of a patient, and FIGS. 2B and 2C are companion simplified views of syringes used in the course of such a procedure.

DETAILED DESCRIPTION OF THE INVENTION

Figure 1:
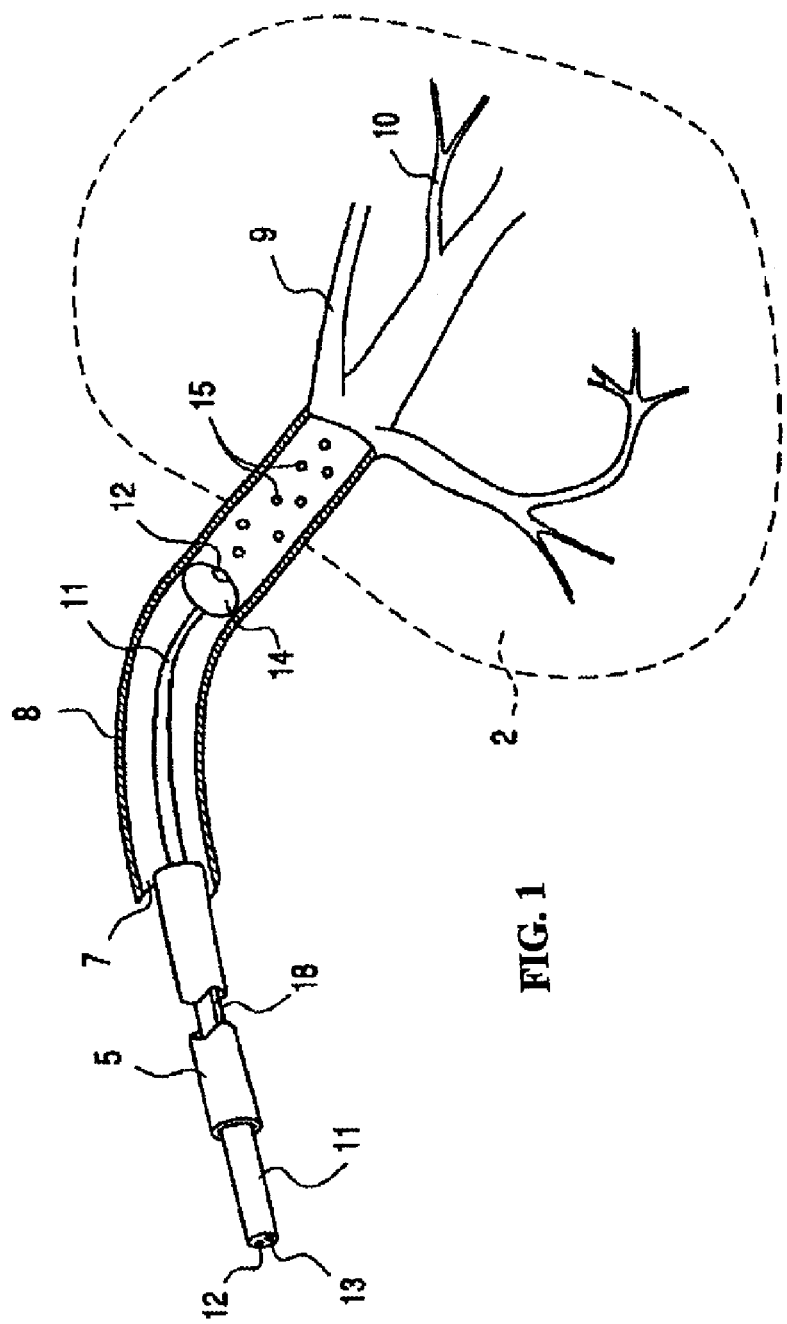
FIG. 1 depicts one embodiment of injection of oncolytic biological agents.

While the making and using of various embodiments of the present invention are discussed in detail below, it should be appreciated that the present invention provides many applicable inventive concepts which can be employed in a wide variety of specific contexts. The specific embodiments discussed herein are merely illustrative of specific ways to make and use the invention and do not delimit the scope of the invention.

A number of human clinical trials using oncolytic viruses have been conducted over the last decade. These trials have involved both systemic intravenous (i.v.) delivery as well as local delivery with the majority employing local (e.g., intratumoral) or regional (e.g., intracavitary or intra-arterial) administration. See Liu T-C and Kirn D. Systemic Efficacy with Oncolytic Virus Therapeutics: Clinical Proof-of-Concept and Future Directions. *Cancer Res.* 67 (2) (2007) 429. Certain embodiments of the present invention are directed to improvements in the prior local and regional delivery by delivering the viral agents with a balloon catheter. The methods disclosed herein exploit the abnormal structure of tumor vasculature.

Although small clumps of nascent tumor cells are able to acquire oxygen and nutrients by diffusion, growth of solid tumors requires formation of new blood vessels for growth. The tumor thus rapidly induces the formation of a dedicated vasculature able to support progression. However, this vasculature features structural and functional abnormalities including: decreased vessel density, heterogeneous microvessel distribution, increased sinusoids, dead ends and arteriovenous anastomosis, and vessels having incomplete basement membranes and absence of smooth muscle. In short, tumor vasculature is characterized by immature, highly-permeable, chaotic vessels with heterogeneous blood flow. The present disclosure applies pressure mediated delivery of oncolytic viruses to the tumor via vessels and ducts leading to the tissue bearing the tumor.

Use of the balloon catheter provides several advantages including selectively local increases in viral concentration, isolation of the delivered viruses from normal fluid flow pressures in the target organ in order to increase contact time and minimize interaction with systemic antibodies; and pressure mediated delivery which allows the viruses to transit the cellular boundary of delivery ducts and vessels and become trapped spongy fluid conduits characterizing the tumor tissue. In one embodiment, the virus is applied in a delivery solution having increased viscosity in order to increase the pressure of delivery and to minimize washout.

The procedure disclosed herein is particularly directed to the requirements of the clinical practice of interventional medicine and thus follows the principle that only those approaches that are both (a) relatively easy to perform, with little or no risk to the patient but a potentially high benefit, and (b) highly cost effective, are likely to be routinely applied in everyday medicine. The approach provided is based on an appreciation by the inventor that biological agents such as viruses are preferably delivered in local concentration to the target tumor area and that such agents need a certain contact time to adhere and migrate from a vascular or ductal bed into the target area.

In preclinical studies, adhesion of the injected viruses and their migration beyond the endothelial barrier may be confirmed by observation after several hours/days of frozen sections using light microscopy and, if desired by electron microscopy. In addition, a marker, e.g., a green fluorescence protein (GFP) may be used as a marker, by introduction of the GFP gene into the viral genome with detection of expressed protein by fluorescence microscopy. Alternatively or in addition, the viruses can be grown in radioactive medium to label their RNA or DNA with radioactive tags that may enable a gross estimate of the concentration delivered to the specific target cancer tissue. Further methods that are more sensitive include detection of viral DNA/RNA by molecular methods including RT-PCR.

The disclosed approach is suitable for delivery of any oncolytic virus, which by definition means viruses that naturally or by design are able to preferentially infect and/or kill cancer cells. To date oncolytic viruses have been identified or developed in members of both DNA and RNA virus families including herpesviridae (i.e. HSV, CMV and pseudorabies), poxviridae, adenoviridae, parvoviridae, rhabdoviridae (i.e. vesicular stomatitis virus), togaviridae (Sindbis) and picornaviridae (i.e. coxsackie virus and poliovirus).

In one embodiment of the invention, the oncolytic virus is a parvovirus. As used herein, the term "parvovirus" includes wild-type autonomous or modified replication competent derivatives thereof as well as related viruses or vectors based on such viruses or derivatives. Parvoviruses are small (25-30 nm) non-enveloped particles containing a 5.1 kb single-stranded DNA genome from which two nonstructural (NS1, NS2) and two capsid (VP1, VP2) proteins are expressed. See Cotmore S F and Tattersall P. "The autonomously replicating parvoviruses of vertebrates" *Adv Virus Res* 33 (1987) 91-174. Some autonomous parvoviruses belong to the category of oncolytic viruses. See Rommelaere J, Cornelis J. "Antineoplastic activity of parvoviruses" *J Virol Methods* 33 (1991)233-51. Several members of the parvovirus genus (H-1PV, MVM, LuIII), whose natural hosts are rodents, are presently under consideration for cancer gene therapy applications due to their failure to transform host cells, capacity for asymptomatic infection of humans, and ability to preferentially propagate in (oncotropism) and kill (oncolysis) neoplastically transformed cells. See Haag A, et al. "Highly efficient transduction and expression of cytokine genes in human tumor cells by means of autonomous parvovirus vectors; generation of antitumor responses in recipient mice" *Hum Gene Ther* 11 (2000) 597-609.

Parvovirus H-1PV has the unique advantage of triggering a distinct death process, at least in brain and some other tumors, namely the cytosolic relocation and activation of lysosomal proteases (cathepsins). See Di Piazza M, et al. "Cytosolic activation of cathepsins mediates parvovirus H-1-induced killing of cisplatin and TRAIL-resistant glioma cells" *J Virol* 81 (2007) 4186-98. As a further advantage, MVMp and H-1PV viruses have been shown to exert oncosuppressive activities in vivo, i.e. they are able to inhibit the formation of spontaneous, chemically or virally induced tumors in laboratory animals. Suitable parvoviruses for purposes of the present invention include but are not limited to rodent parvovirus species H-1PV, LuIII virus, various strains of Minute virus of mice (MVM) (recently renamed mice minute virus (MMV)), including MVPi and MVPp, Mouse parvovirus (MPV), Rat minute virus (RMV), Rat parvovirus (RPV) or Kilham Rat virus (RV).

The oncolytic viruses are delivered in an effective dose and combined with a pharmaceutically acceptable carrier. An "effective dose" refers to amounts of the active ingredients that are sufficient to affect the course and the severity of the disease, leading to the reduction or remission of such pathology. An "effective dose" useful for treating and/or preventing these diseases or disorders may be determined using methods known to one skilled in the art. "Pharmaceutically acceptable" is meant to encompass any carrier that does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

"Effective extravasation pressure" means a pressure sufficient to exceed the normal fluid pressure of a given lumen and cause fluids to be forced between cells forming the lumen walls and thereby overcome the so called endothelial barrier consisting of endothelial cells and the basal membranes of the vessel or duct. Because of the abnormal vasculature of tumor tissue, tumor tissue is particularly susceptible to pressure mediated delivery. In one embodiment, the oncolytic virus formulation includes a marker such as a dye or radiomarker that can be visualized during administration with adjustment of extravasation pressure to assure effective perfusion of the administered agent into the tumor and immediately surrounding tissue. In one embodiment, the marker is a nuclear tracer such as Tc-99 or a MRI sensitive agent such as Gadolinium or derivatives thereof, and small superparamagnetic particles such as iron oxide nanoparticles. Typically, a change in pressure of 20 mm Hg is sufficient to overcome the endothelial pressure in normal tissue. Visualization of the delivery process permits adjustment of delivery pressure to achieve desired perfusion of the tumor tissue.

Additional aspects include the delivery of oncolytic viruses together with, or delivered in the same procedure with, other means to enhance the effectiveness of the administration and treatment. Non-limiting examples of additional agents include natural cytotoxic and cytostatic agents such as interferons or chemical compounds inducing cytotoxic/static effects. For these agents, the same principal of overcoming the endothelial barrier with pressure is applied to selectively enhance delivery to the region of the tumor.

Aspects of the invention include a method for treating cancer in a patient's body, which comprises delivering oncolytic viruses, such as oncolytic parvoviruses, locally to a tumor by an intraluminal application through a blood vessel or duct, and, preferably, occluding the blood vessel or duct proximal to the location of desired delivery of the oncolytic agent during at least a portion of the duration of delivery to increase the concentration of oncolytic agent delivered to the target site. The intraluminal application of oncolytic agents through a blood vessel may be performed through an arterial or venous vessel.

Preferably, a balloon catheter is employed for the intraluminal application, and occlusion of the blood vessel or duct is performed by inflating the catheter's balloon for a time interval prescribed to increase the concentration of oncolytic agents delivered to the target site. Further aspects of the invention include the injection of other therapeutics together with the oncolytic viruses in order to enhance and boost the oncolytic effects of the viruses alone. Such therapeutics include cytostatic drugs, interferons and stem cells. In one embodiment, the stem cells are autologous mesenchymal derived cells with or without further modifications. Such modifications include genetic modifications of the stem cells to overexpress or suppress certain cellular genes and connected protein expression, thereby altering the function of the cells. Blocking peptides, aptamers and antibodies are additional therapeutic agents to be considered for injection through the same delivery route in conjunction with the oncolytic viruses.

Use of the balloon catheter allows delivery by either normal or supranormal pressure. Typically, bolus injection will result in supernormal pressure within an artery, vein or duct. The term "supernormal" in this context means pressure in excess of the normal range of fluid pressure within the respective artery, vein or duct. Supernormal pressure may be expected to force fluid including the oncolytic viruses into the intercellular space between cells lining the blood vessel or duct. Where constant infusion is performed, the pressure may be adjusted to either exceed normal pressure or to be similar to normal pressure. Use of extranormal pressure including by retrograde delivery has been applied to delivery of B-blockers and calcium antagonists into ischemic myocardial tissue via the coronary veins. Likewise this approach has been applied to delivery of gene therapeutic agents including viral vectors into normal tissue. For example, Boekstagers et al. employed pressure regulated retrograde delivery of an adenovirus vector encoding a reporter gene into the myocardium via the coronary vein. ("Myocardial gene transfer by selective pressure-regulated retroinfusion of coronary veins" Gene Therapy 7 (2000) 232-240). The pressure employed was designed to achieve a preset retroinfusion pressure 20 mmHg higher than the systolic plateau of coronary venous occlusion pressure using a balloon catheter inflated to a pressure of 150 mmHg maintained constantly throughout the retroinfusion treatment.

One embodiment of the present invention is directed to a novel delivery method that applies pressure mediated viral delivery in two unique contexts: the delivery of oncolytic viruses that selectively replicate in and destroy tumor tissue, and the delivery to tumor tissue in such a way that regional high concentrations of virus are assured. In this regard, emerging clusters of tumor cells, which may include millions of cells, are too small to be individually perceived and targeted by intratumoral injection. Prior intratumoral injection of oncolytic viruses may not permit exposure of the viruses to all of the foci of tumor cells in a given organ. As such, it is important to apply the oncolytic agent as broadly as possible in the region of the tumor while localizing the viruses in the area for sufficient time to achieve attachment and thus infectivity of the viruses. In this context, while the tumor vasculature and the endothelial lining of ductal structures in a tumor is abnormal, such abnormality can be harnessed to the advantage of efficient viral delivery concentration to tumor cell clusters.

In some aspects of the invention, the method further includes introducing a guide wire through the blood vessel to the target site, and thereafter advancing the catheter over the guide wire until the distal end of the catheter reaches a selected point in the vicinity of the target site for delivering the oncolytic agents.

Reference will now be made to the accompanying figures in describing exemplary processes. It should be noted at the outset that the figures are not intended to be to scale, nor to do more than serve as a visual aid to the description. In those figures representing the human body or body parts, certain components may be exaggerated relative to others for the sake of emphasis or clarity of the respective accompanying description.

Referring to FIG. 1, in one embodiment, oncolytic agents are applied to the donor patient by first introducing a balloon catheter 11 into the vascular system, e.g., at the patient's groin using an introducer, and through a guiding catheter 5 over a guide wire 18 into the orifice 7 of a vessel or duct 8 at or in the vicinity of the cancer tissue to be treated. In the depicted example, the tumor 2 is supplied with blood through artery 8 and its distal branches 9 and 10. The oncolytic agent is injected through the inner (central) lumen 12 of the balloon catheter 11 by hand injected or by means of a motor driven constant speed injection syringe that is connected to entry point of the central lumen at the proximal end of catheter 11. The exit point of the central lumen 12 is at the distal end of catheter 11 which has been advanced into the artery 8 in proximity to the site of the desired treatment. The oncolytic agents 15 are thereby delivered to this site by means of infusion over 10 seconds to 30 minutes, for example. The disclosed delivery method overcomes several problems with prior vascular delivery schemes. During transit through the vascular system, bloodborne viruses are susceptible to binding by antibodies that normally participate in inactivating viruses and removing them via the reticuloendothelial system. Furthermore any particles transiting a blood vessel or duct, including viruses, are normally separated from the parenchymatous organ or the tissue outside the vessel by the continuous cells lining the vascular or ductal conduit. Intravenously delivered oncolytic agents would be separated from the cancer tissue to be treated by the endothelial lining and other tissue layers of blood vessels that lead to the cancer tissue. However, under certain circumstances this barrier is overcome, and the agents can attach to the inside of the vessel, migrate and proliferate in the adjacent tissue. Here an increase in pressure with increasing injection volume following the balloon inflation in the distribution zone can overcome the endothelial layer and effect extravasation out of the vascular system.

The process disclosed herein further provides for maximal numbers of the viral agents to contact the cancer tissue without dilution. Use of the balloon catheter 11 or some other mechanism allows for selective blockage of the antegrade blood flow and loss of the agent into the systemic circulation. A balloon catheter is preferred because it is a well known, often used and reliable device for introduction to a predetermined site in a vessel such as an artery or vein. In the process of the invention, the balloon 14 of catheter 11 is inflated with biocompatible fluid through a separate lumen 13 of catheter 11 to occlude artery 8 and its distal branches 9 and 10, thereby causing perfusion through the vessel to cease. Inflation of the balloon may be commenced immediately before or at the time of injection of the oncolytic agent through the inner lumen of the catheter, and is maintained throughout the period of injection. This enables adhesion of a desired large number of infectious agents to the target tissue. The absence of blood flow at the delivery site has several advantageous effects. It prevents what would otherwise result in a retrograde loss of injected agents as well as antegrade dilution with blood flow while providing an ability to increase the pressure at the injection site to overcome the endothelial barrier and to force the viruses into the sub-endothelial tissues.

Dependent on location of the balloon, the type of vessel or duct, the type of organ injected into, and the multiplicity of viral agents delivered, the blockage is maintained for a relatively short period of time, preferably on the order of one to fifteen minutes, and in any event sufficient to allow a high concentration and considerable number of viral attachments to the cancer tissue at the designated site. In the case of a slow infusion of the oncolytic agents, the period of blockage is maintained longer by steady inflation of the balloon over the injection period, for example up to about 30 minutes, for enhancement of contact and adherence to the endothelium. The balloon is deflated, and the balloon catheter is removed from the patient after the procedure.

The concept of the present embodiment is to use the natural distribution tree of the arterioles and the capillaries or the ductal distribution tree to cover the complete inner, medial and outer layers of the cancer tissue with oncolytic agents.

The method is not limited to particular cancers as long as the requirements listed above are fulfilled. Rather, the process by which the treatment is performed may be applied to the brain, e.g., in case of glioma. In this case, the injection catheter is advanced to the site of the cancer tissue through an appropriate arterial path into the applicable region of the patient's brain, as described more fully below. Blockage of blood flow in this case would add a period (e.g., minutes) of limited blood supply but would enable the oncolytic agents to overcome the endothelial barrier.

Other possible cancers to be treated by the process disclosed herein include cancer of the pancreas, the liver, and the kidneys. The pancreas has a duct (the ductus Wirsungii) through which pancreatic enzymes are delivered into the intestines, and which can be accessed in a retrograde manner by endoscopic retrograde choledocho-pancreaticography (ERCP). By means of the visual guidance, such as through a small fiber optic instrument, a small balloon catheter may be introduced into this duct, and the balloon inflated to occlude the duct during delivery of oncolytic agents through the catheter's inner lumen to the site of the cancer tissue, so as to prevent the injected agents from being washed out into the intestines and thereby enhancing adhesion and penetration by a relatively large number of the administered agents. An analogous procedure is used for treatment of cancer tissue of the liver, through the bile duct system. Here also, it is important to overcome the barrier of the normal bile duct with pressure that can be generated only if the balloon is inflated while the agents are slowly injected. The pressure distal to the injection site increases as more and more volume is injected. Treatment of cancer tissue in the kidney(s) may be conducted by an analogous procedure.

In one embodiment of the invention, effective delivery of the oncolytic viral agent is visualized concurrently. In one embodiment of delivery to the bile duct, intraoperative cholangiography is performed to visualize the anatomy of the duct system as well as effective delivery of the viral agent. In one embodiment, the viral agent is formulated with a dye such as a fluorescent dye that can be visualized such as with the same fiber optic guidance system that is used to introduce the balloon catheter into the duct or vessel. In one non-limiting example of a visualization system that may be employed, a dye visible at a wavelength of 750 nm or greater is used together with an exciting light source such as that as disclosed in U.S. patent application Ser. No. 11/508,734, published as 2007/0244,367, incorporated herein by reference. Further examples of a visualization systems are disclosed in U.S. patent application Ser. No. 11/868,432, published as US 2008/0249,400, and incorporated herein by reference. Other imaging methods include SPECT, CT and MRI together with their respective enhanced visualization agents.

Brain Cancer:

FIG. 2A is a diagram useful to describe an example of a method for delivery of oncolytic agents through a balloon-guided catheter to the anterior cerebral circulation in a patient 31. An introducer sheath 33 of appropriate size, typically 5-7 French, is advanced through the right groin 32. Then a balloon guided double lumen catheter 34 is advanced through introducer sheath 33 and over a small guide wire 48 directed to the artery of interest. Guide wire 48 has a diameter in a range of 0.014 to 0.018 inches, and a flexible distal tip to render it bendable so as to direct the guide wire through the vessel to the vicinity or locality of the selected target site. The proximal end of guide wire 48 is left to project from opening 35a of catheter 34. A side branch opening 35b of catheter 34 is operatively coupled through an inflation lumen of the catheter for selective inflation and deflation of its balloon 46.

Initially, guide wire 48 is advanced through the central lumen of catheter 34. The catheter may then be manoeuvred to the selected site by gliding it over the guide wire through iliac artery 37, abdominal and thoracic aorta 38, through the aortic arch 39, and into the right carotid artery 40 beyond the branching off of the vessels 41 for the right arm. As an alternative, guide wire 48 and catheter 34 may be advanced to a location in the left carotid artery 42. The left carotid artery either originates after the branch-off of the left subclavian artery 43, or directly from the aortic arch 39 where the left subclavian artery originates from a separate orifice in the aortic arch. After advancing guide wire 48 through the common carotid artery into the right internal carotid artery 40 and into the proximal circulation of the circulus willisi 44, the anterior cerebral artery 45 is encountered at its origination. Alternatively, in lieu of access through the femoral artery, vascular access to the carotid may be obtained through the right radial artery, particularly in patients with a strong radial pulse.

After the catheter 34 has been advanced so that its tip 47 and balloon 46 are positioned in the anterior cerebral artery 45, with the catheter tip 47 located at the site to which the parvoviruses are to be delivered, guide wire 48 is removed. The opening 35a of the same lumen that had been used for the guide wire is now available for injecting oncolytic agents. Toward that end, and with reference now also to FIGS. 2B and 2C, the conus 50 of a syringe 49 (FIG. 2B) is connected to port 35a of catheter 34, and the conus 53 of another syringe 52 (FIG. 2C) is connected to the inflation port 35b of catheter 34. Port 35b operates through the inflation lumen for balloon 46 of catheter 34. Syringe 52 is typically of small size and includes a pressure gauge 55 to measure the applied pressure as the fluid 54 within the syringe is expelled into port 35b to inflate balloon 46 to a low pressure of 0.5 to 0.8 atm. This pressure is sufficient to tightly seal the vessel (anterior cerebral artery 45) at the location of the balloon. To assist in recognizing a possible rupture of balloon 46, the fluid 54 in syringe 52 may be a 50/50 mixture of saline and contrast dye. Balloon 46 may be deflated at the completion of the procedure or in the event of an emergency by withdrawing the fluid 54 back into syringe 52.

While anterior cerebral artery 45 is tightly sealed toward its proximal end 44, oncolytic agents 51 within syringe 49 are slowly ejected from conus 50 into port 35a of the catheter. The agents travel through the central lumen of catheter 34 formerly occupied by guide wire 48 and exit the lumen at the site of catheter tip 47. The agents are thus delivered for entry into the cerebral circulation at that site. As noted earlier herein, the very brief period of limited blood supply during blockage of blood flow through the anterior cerebral artery 45 by inflated balloon 46 is sufficient for viral agents to overcome the endothelial barrier but not enough to cause injury to the brain. Repetitive injections with the allowance of intermittent blood flood may be employed to as one means to increase the total virus load to the treatment site.

Renal Cancer:

For treating cancer of the kidneys, an oncolytic agent may be introduced in a similar manner through a catheter navigated over a guide wire in the patient's right groin into the iliac artery 37, the abdominal aorta 38, the applicable renal artery 57, and the diseased kidney 58.

Figure 3:
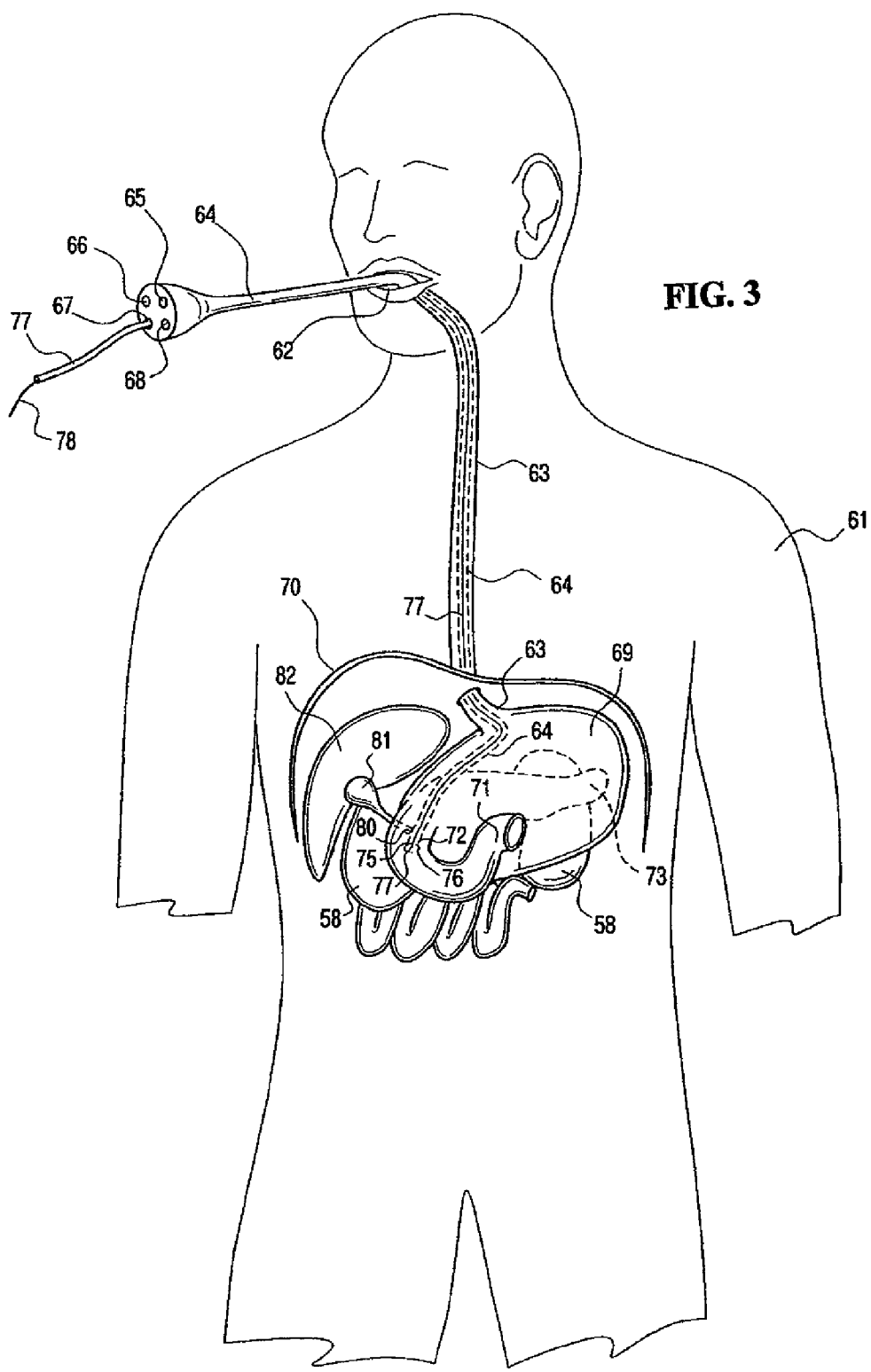
FIG. 3 is a transparent front view of a patient illustrating an exemplary procedure for applying oncolytic biologic agents through a duct of a patient's body, to cancer tissue of an organ such as the pancreas or liver.

Ductal Delivery:

If ductal delivery is desired, FIG. 3 is a diagram useful to describe an example of a method for delivery of oncolytic agents through a natural duct in a patient 61. In this exemplary procedure, an endoscope 64 is advanced through the mouth 62 and esophagus 63 of the patient. The endoscope 64 is flexible, and is designed and implemented with a plurality of channels including, in this illustrative embodiment, visualization and fiber optics channel 65, flushing channel 66, side port open channel 67, and working channel

68. The distal tip 75 of endoscope 64 is readily bendable to allow the endoscope to be advanced through a tortuous path. During the procedure the patient may be give a local anaesthetic to prevent gagging. The endoscope 64 is advanced via the esophagus 63 through the diaphragm 70, into and through the stomach 69, and further until its distal tip is located in the duodenum 71.

Pancreatic Cancer:

If the pancreas is target organ to be treated, the location of the distal tip should be such that a side port 72 of the endoscope adjacent its distal tip is aligned for entry into the ductus Wirsungii 76, which supports the internal structure of the pancreas 73 with all its side branches. Proper alignment may be verified through the visualization and fiber optics channel 65 of endoscope 64. Then, a small balloon guided catheter 77 (e.g., 2.7 French outer diameter) is advanced over a guide wire 78 threaded through the side port open channel 67 and out of the side port 72 into the ductus Wirsungii. Oncolytic agents are delivered and the balloon is inflated by the use of syringes in a method similar to that described with respect to FIGS. 2B and 2C. The distal tip of the catheter is advanced through channel 67 of the endoscope 64 and out of the side port 72 to the site of the pancreatic tissue to be treated. The catheter's balloon is then inflated through the inflation lumen of the catheter to occlude the Wirsungii duct while oncolytic agents are introduced into the pancreatic tissue through the central lumen of the catheter which is now open following removal of the guide wire. By proper positioning of the catheter's distal tip at the site of the cancer tissue, the agents are delivered locally in high concentration. Occlusion of the duct precludes the agents from washing out into the intestines, so as to enhance large scale adhesions and penetration of the agents into the target tissue.

Liver Cancer:

Blood enters the liver from both the hepatic artery and the hepatic portal vein. Oxygenated blood is carried via the hepatic artery into the sinusoids of the liver. Deoxygenated blood and nutrients from the digestive system are via the portal vein into the sinusoids of the liver, which are lined by plates of liver (hepatic) cells. Blood leaves the liver first through the sinusoids and into the central vein of each lobule before finally leaving the liver through the hepatic vein. Bile produced by the liver cells lining the sinusoids leaves the liver first through the bile canaliculi and ultimately through the bile duct. Thus, compounds delivered to the liver may be considered to be delivered with the normal direction of flow (antegrade) if delivered through the hepatic artery or the hepatic portal vein and against the normal direction of flow (retrograde) if delivered through the hepatic vein or through the bile duct. Retrograde delivery through the bile duct can be accomplished endoscopically as is done with contrast dyes in ERCP procedures (Endoscopic Retrograde Cholangiopancreatograpy) or percutaneously as in PTCA procedures (Percutaneous Transhepatic Cholangiography).

As depicted in FIG. 3, for retrograde ductal delivery, the distal tip 75 of endoscope 64 is positioned in the duodenum 71 such that its side port 72 is aligned for entry into the common biliary duct 80, which supports the liver 82 and the gall bladder 81. As an alternative, the side branch of the bile duct may be used. The guide wire and balloon catheter are fed through channel 67 and out of side port 72 of the endoscope, into the duct. The distal tip of the catheter is positioned at the target site of the liver tissue, the guide wire is removed, and the catheter's balloon is inflated to occlude the biliary duct during the introduction of the agents. The oncolytic agents are injected through the central lumen of the catheter for adhesion to and engraftment within or in proximity to the tumor.

Administration and Co-Administration of Cytokines:

In one embodiment, the oncolytic viruses are co-administered by local catheter delivery together with one or more interferons ("IFN"). As used herein, the term interferons refers to the cytokine class molecules that are notably species specific but induce antiviral states that are not viral type specific. Encompassed in the term are all interferons including type I (IFN-α, IFN-β and IFN-ω) and type II (IFN-γ) interferons. Also encompassed are the type III interferons (IFN-λ), which are classified as interferon by some on the basis of anti-viral activity but are otherwise classified as interleukins (IL-28 and -29).

A number of different interferons are commercially available including Roferon-A (IFN-α-2a), Intron-A (IFN-α-2b), Infergen (IFN-alfacon-1, a consensus IFN-α differing by 18 amino acids from IFN-α-2a and 19 amino acids from IFN-α-2b), Multiferon (IFN-α-Le, a natural IFN-α obtained from human leukocytes), Alferon-N (IFN-α-n3), Avonex (IFN-(β1a), Betaseron (IFN-β1b), and Actimmune (IFN-γ-1b). Currently available interferons are, depending on the indication, given intramuscularly, intravenously, or subcutaneously on a daily or three times a week basis. Pegylated interferons, including Peg-Intron (pegylated IFN-α-2b) and Pegasys (pegylated IFN-α-2a), have been developed to increase the normally short pharmacologic half-life of interferons and are injected once weekly, rather than three times per week for conventional interferon-alpha.

Interferons were initially approved to treat viral infections including in particular chronic hepatitis B and C. Several interferons have now been approved for treatment of certain cancers. For example, interferon α-2a (Roferon-A) is FDA-approved to treat hairy cell leukemia, AIDS-related Kaposi's sarcoma, and chronic myelogenous leukemia and is being evaluated in a number of other cancers.

Among other things, including upregulation of MHC I and therefore increased presentation of self and altered self antigens to cytotoxic T lymphocytes, IFN-α/β have been recently shown to result in increased p53 activity in stressed cells. Expression of p53 promotes apoptosis or programmed cell death and may form a basis for the observed usefulness of IFN-α/β against some cancers. See Takaoka A, et al. "Integration of interferon-α/β signalling to p53 responses in tumour suppression and antiviral defence" *Nature* 424 (2003) 516.

It has recently been determined that systemic interferon administration is able to greatly potentiate the ability of oncolytic parvoviruses to reduce the tumor burden in an animal model of advanced pancreatic cancer. However, systemic interferon administration, whether by intramuscular injection or intravenous infusion is associated with considerable malaise. Indeed, the severe symptoms of flu virus infection in humans are largely mediated by the interferons induced by the viral infection. Interferons are largely responsible for the flu symptoms of fever, chills, fatigue, headache, and muscle pain. Other common side effects include diarrhea, nausea, vomiting, abdominal pain, joint aches, back pain and dizziness. Other possible side effects include anorexia, congestion, increased heart rate, confusion, low white blood cell count, low platelet count, low red blood cell count, an increase in liver enzymes, an increase in triglycerides, temporary skin rashes, mild hair loss or hair thinning, edema, cough or difficulty breathing. The severe side effects of systemic interferon administration have heretofore limited the use of interferons in cancer therapy and eventually in therapy of advanced stages of hepatitis.

In accordance with one embodiment provided herein, the above described problems associated with interferon administration are reduced or eliminated by providing the interferon directly to the organ affected with the tumor using a catheter. In one aspect, the interferon is co-administered together with the oncolytic viruses using a catheter as disclosed above with reference to various specific cancers including, without limitation, pancreatic cancer, prostate carcinoma, lung cancer, renal cancer, liver cancer, lymphoma, breast cancer and brain tumors. Using catheter delivery, including via natural vessels and/or ducts leading to or from the affected organ, the concentration of interferon can be locally higher than that which can be safely obtained by systemic administration.

Certain oncolytic agents, including certain of the parvoviruses, replicate readily in tumor tissues while sparing normal cells. However, with other oncolytic viruses, the tropism for cancer cells is relative and normal cells are also infected. In certain tumors, interferon signalling is disrupted, which is a possible mechanism for the apparently increased virulence of oncolytic viruses in tumor cells compared to normal cells having intact interferon pathways. In one aspect of the invention where oncolytic agents are used that are able to replicate in normal cells, the co-administration of interferon protects normal cells surrounding the tumor from infectivity without reducing the sensitivity of the tumor cells to the effects of the oncolytic agent.

In other aspects, interferons are administered in conjunction with oncolytic viral therapy. By conjunction it is meant near the time of viral administration. The interferon may be administered at several time points including one or more of before, during and after delivery of the virus. For example, the interferon may be provided by loco-regional delivery from one to several days prior to infusion of the virus and may be further provided after viral administration for as long as the virus continues to replicate. In one aspect, loco-regional delivery of interferon to the cancer area is through one or more of the vascular tree of arteries, arterioles, capillaries, post capillary venules and veins, and/or the respective ductal system of the organ that supplies fluids to or drains the cancer area.

In other aspects, loco-regional delivery of interferon is provided by catheter delivery to the liver for treatment of hepatitis. In one embodiment, the interferon is provided in a slow release form. For example, the interferon may be encapsulated within a liposome or other wise localized or trapped within the tissue for continued release over a period of time. In other embodiments, an arterial catheter is placed via the gastroduodenal artery in the hepatic artery for the periodic scheduled delivery of interferon loco-regionally over a prolonged period. Locally high interferon concentrations are in some instances augmented by delivery of antiviral medications orally or by intravenous delivery.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements and that the invention shall be limited only by the appended claims and the rules and principles of applicable law.

I claim:

1. A method for treating cancer tissue in an organ, said method comprising delivering an oncolytic virus selected for susceptibility of infecting the cancer tissue to be treated, locally to the cancer tissue in the organ by application of the virus proximally through an infusion lumen of a balloon catheter inserted into a blood vessel or duct in direct fluid communication with a target site of the cancer tissue, and discharging the virus under relatively low pressure distally from the infusion lumen directly into the blood vessel or duct proximally of the site and distally of a single balloon of the catheter; while selectively increasing pressure in the blood vessel or duct by the concentration or volume of virus delivered, to force the virus under an effective extravasation pressure through a natural endothelial barrier of the blood vessel or duct lining and into the cancer tissue at the target site, thereby increasing local delivery of an effective dose of the virus to the target site of the cancer tissue.

2. The method of claim 1, further comprising occluding said blood vessel or duct proximal to a location of discharge of the oncolytic virus by inflating the single balloon during at least a portion of the duration of said delivering of said oncolytic virus to increase the concentration or volume of virus delivered to said site distally of the inflated balloon.

3. The method of claim 1, wherein the application of oncolytic virus through the catheter lumen directly into a blood vessel is performed through an arterial vessel.

4. The method of claim 2, comprising performing said occlusion of the blood vessel or duct by inflating the single balloon through an inflation lumen of said catheter distinct from the infusion lumen for a prescribed time interval sufficient to enable increase of the concentration or volume of oncolytic virus delivered to said site by said effective extravasation pressure, but insufficient to damage healthy tissue.

5. The method of claim 4, including introducing a guide wire through said blood vessel or duct to said site and thereafter advancing said catheter over the guide wire until the distal end of the catheter reaches a selected point in the vicinity and proximally of said site for delivering the oncolytic virus thereto.

6. The method of claim 1, wherein said cancer belongs to the group of pancreatic cancer, prostate carcinoma, lung cancer, renal cancer, liver cancer, lymphoma, breast cancer or a brain tumor.

7. The method of claim 1, wherein said oncolytic virus is a H1 parvovirus (H1-PV) or a related rodent parvovirus.

8. The method of claim 7, wherein said related rodent parvovirus is LuIII, Mouse minute virus (MMV), Mouse parvovirus (MPV), Rat minute virus (RMV), Rat parvovirus (RPV) or Rat virus (RV).

9. The method of claim 1, wherein the oncolytic virus is formulated together with a contrast agent and the delivery is monitored with adjustment of the delivery pressure to maximize deposition through the natural endothelial barrier presented by the blood vessel or duct lining at the site of the cancer tissue.

10. A method for delivering parvoviruses to a tumor in a patient's body, said method comprising delivering parvoviruses to the site of the tumor to be treated by an intraluminal application of the parvoviruses through a central lumen of a single-balloon catheter inserted into a blood vessel or duct of said site using an effective extravasation pressure that results in selective delivery of an effective dose of the parvoviruses from a distal exit of the catheter central lumen directly through a natural endothelial lining of the blood vessel or duct and into a parenchyma at the site of the tumor located distally of said distal exit, after having inflated the single balloon of the catheter located proximally of said distal exit.

11. The method of claim 10, further comprising occluding said blood vessel or duct by the balloon inflation proximal to the location of parvovirus entry into parenchyma at the tumor site via said intraluminal application during at least a portion of the duration of said delivery of parvoviruses to increase the concentration or volume of parvoviruses, whereby to produce said effective extravasation pressure to enable said effective dose to be delivered to said site.

12. The method of claim 10, further including administering one or more interferons locally together with the parvoviruses to increase the concentration or volume of parvoviruses, and thereby of said effective extravasation pressure to enable an effective dose of parvoviruses to be delivered to said site.

13. The method of claim 11, further including administering one or more interferons locally together with the parvoviruses to assist in increasing concentration or volume of parvoviruses in production of said effective extravasation pressure to enable an effective dose to be delivered to said site.

* * * * *